US00PP31507P2

(12) United States Plant Patent
Karniel

(10) Patent No.: US PP31,507 P2
(45) Date of Patent: Mar. 3, 2020

(54) SEEDLESS TABLE GRAPE (GRAPEVINE) NAMED 'ARRATWELVE'

(50) Latin Name: *Vitis vinifera*
Varietal Denomination: ARRATWELVE

(71) Applicant: AGRICULTURAL RESEARCH AND DEVELOPMENT LIMITED LIABILITY COMPANY, Bakersfield, CA (US)

(72) Inventor: Shachar Karniel, Bakersfield, CA (US)

(73) Assignee: Agriculture Research and Development Limited Liability Company, Bakersfield, CA (US)

( * ) Notice: Subject to any disclaimer, the term of this patent is extended or adjusted under 35 U.S.C. 154(b) by 0 days.

(21) Appl. No.: 16/350,855

(22) Filed: Jan. 23, 2019

(51) Int. Cl.
*A01H 5/08* (2018.01)
*A01H 6/88* (2018.01)

(52) U.S. Cl.
USPC ..... Plt./205

(58) Field of Classification Search
CPC ..... A01H 5/08
See application file for complete search history.

*Primary Examiner* — Annette H Para
(74) *Attorney, Agent, or Firm* — Lewis Roca Rothgerber Christie LLP

(57) ABSTRACT

A new distinct variety of grapevine named ARRATWELVE abundantly forms attractive meaty and juicy seedless berries with a red skin coloration; in medium-to-large clusters which display a sweet and natural flavor. The fruit commonly is ready for harvesting during August in San Joaquin Valley of Central California, U.S.A, and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has a varietal denomination 'ARRATWELVE'.

BACKGROUND OF THE INVENTION

A breeding program was initiated during the late 90's near Bakersfield in San Joaquin Valley of Central California. In 2004, during this breeding program, a new variety of *Vitis vinifera* was created by deliberate cross breeding of two parent plants by emasculation of the pollen bearing organ of the female and introducing pollen from another male origin. The female parent of the new variety was ARRA RED. which is a mid-season red grape variety with thin skin and a natural flavor (non-patented in the United States). The male parent (i.e. the pollen parent) of the new variety was JE1, a fire red vigorous variety with a light Muscat flavor (non-patented in the United States).

TABLE 1

ARRATWELVE compared with parents & closely related variety:

| | ARRATWELVE | ARRA Red | JE1 | Flame |
|---|---|---|---|---|
| Seed Trace | sterile | large | small | small to none |
| Bunches per vine | 48 | 42 | 32-36 | 28-36 |
| Berry Color | red | red | Fire-red | grayish red |

The parentage of the new variety can be summarized as follows:

ARRA RED X JE1

An artificial pollination was created, and the result was an embryo which possessed unique genetic qualities. The rudiments resulting from the above pollination were embryo rescued.

In 2005 the plant was transplanted to Bakersfield in San Joaquin Valley of Central California.

It was found that the new grapevine of the present invention possesses the following combination of characteristics:

(a) Forms attractive meaty and juicy seedless berries with a red skin coloration; in medium-to-large clusters which display a sweet and natural flavor, (b) Commonly bears fruit during the month of August in the San Joaquin Valley of Central California, U.S.A., and (c) Bears fruit that is firm and is well amenable for storage, handling, and shipping.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2006 near Bakersfield in the San Joaquin Valley of Central California, U.S.A. by bud grafting on mature Thompson rootstock (non-patented in the United States). Such asexual propagation has been conducted thereafter in successive years to date and has shown that the characteristics of the new variety are strictly transmissible from one generation to another. Accordingly, the new variety undergoes asexual propagation in a true to type manner.

SUMMARY OF THE INVENTION

The new variety ARRATWELVE is a medium size, red seedless table grape with a high production, e.g., about 48 bunches per vine, and an average of about one to two bunches per shoot.

Asexual reproduction by micro propagation of the new variety as performed near Bakersfield, Calif., U.S.A., shows that the forgoing and other distinguishing characteristics come true to form and are established and transmitted through succeeding propagations.

BRIEF DESCRIPTION OF THE DRAWINGS

The accompanying photographic illustration shows typical specimens of vegetative growth of six-year-old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRATWELVE'

DETAILED BOTANICAL DESCRIPTION

The chart used in the identification of colors is The R.H.S. Colour Chart of The ROYAL HORTICULTURAL SOCIETY (3$^{rd}$ Edition). The description is based on the observation of plants growing on 'Thompson Seedless' rootstock outdoors near San Joaquin Valley of Central California, U.S.A.

Vine:

*Vigor*.—Vigorous upright shoots.

*Productive capacity*.—Bearing at a natural, average capacity. Spur pruning.

*Trunk*.—Strong and developed. Diameter is 2.8" at 13" above ground. Rough with a fibrous, shaggy exterior. Light maple brown coloring (grayed orange 166 D).

Time of bud burst: March 7$^{th}$ in Bakersfield, Calif.

Young shoot:

*Openness of tip*.—Half open.

*Prostrate hairs on tip*.—Absent or very sparse.

*Anthocyanin coloration of prostrate hairs on tip*.—Absent or very weak.

*Erect hairs on tip*.—Sparse.

Young leaf:

*Color of upper side of blade*.—Green with anthocyanin spots (yellow green 152A).

*Prostrate hairs between main veins on lower side of blade*.—Dense.

*Erect hairs on main veins on lower side of blade*.—Medium.

Shoot:

*Attitude* (*before tying*).—Semi-erect.

*Color of dorsal side of internodes*.—Red.

*Color of ventral side of internodes*.—Green.

*Color of dorsal side of nodes*.—Red.

*Color of ventral side of nodes*.—Green and red.

*Erect hairs on internodes*.—Absent or very sparse.

*Length of tendrils*.—Long.

*Color of tendrils*.—Yellow green 152 B.

*Number of tendrils*.—3.

Flower:

*Sexual organs*.—Fully developed stamens and fully developed gynoecium.

Mature leaf:

*Size of blade* (*inches*).—Medium (5.5"×5").

*Shape of blade*.—Wedge-shaped.

*Blistering of upper side of blade*.—Absent or very sparse.

*Number of lobes*.—Five.

*Depth of upper lateral sinuses*.—Medium.

(*Only varieties with lobed leaves*).—Arrangement of lobes of upper lateral sinuses: Closed.

*Arrangement of lobes of petiole sinus*.—Half open.

*Length of teeth*.—Medium.

*Ratio length/width of teeth*.—Medium.

*Shape of teeth*.—Both sides straight.

*Proportion of main veins on upper side of blade with anthocyanin coloration*.—Low.

*Prostrate hairs between main veins on lower side of blade*.—Absent or very sparse.

*Erect hairs on main veins on lower side of blade*.—Absent or very sparse.

*Length of petiole compared to length of middle vein*.—Moderately shorter.

*Top side color*.—Green 137 B.

*Bottom side color*.—Yellow green 146 B.

*Texture*.—Relatively smooth.

*Vein color*.—yellow-green 146 D.

*Petiole length*.—2.2".

*Petiole diameter*.—0.1".

*Petiole color*.—Red purple 59-B.

*Base descriptors*.—Cordate.

*Leaf margin*.—Doubly Serrate.

*Leaf apex*.—Accuminate.

Reproductive organs:

Stamen:

*Color*.—Yellow-green 144-B.

*Size*.—0.00394".

Time of beginning of ripening: August 15$^{th}$ in Bakersfield, Calif.

Bunch:

*Size* (*peduncle excluded*).—Medium.

*Density*.—Medium.

*Length of peduncle of primary bunch*.—Medium.

*Average bunch weight*.—1.13 lbs.

Berry:

*Size*.—Large.

*Length*.—1.2".

*Weight*.—0.25 oz.

*Diameter*.—0.8".

*Shape*.—Obloid.

*Color of skin* (*without bloom*).—Red.

*Ease of detachment from pedicel*.—Moderately easy.

*Thickness of skin*.—Thin.

*Anthocyanin coloration of flesh*.—Strong.

*Firmness of flesh*.—Moderately firm.

*Particular flavor*.—None.

*Formation of seeds*.—None.

*Market use of observed plant*.—Fresh market.

*Berries per bunch*.—170.

Woody shoot:

*Main color*.—Dark brown.

Age and growing conditions: Six years growing under Y system in South Joaquin Valley (hot, dry summers).

Shipping characteristics:

(E.g. number of days fruit has been stored under specific conditions): Fruit was in cold storage. Stored in poly bags inside Styrofoam boxes with sulfur pads. After 60 Days: rachises were 75% green; 2% berry shuttering; no berry wrinkling or cracks were apparent.

DNA profile: To further the characterize the new variety DNA was extracted from plant samples and a DNA profile was obtained at California Seed & Plant Lab, California USA using base pairs for 10 standard microsatellite DNA markers. The data is presented hereafter.

TABLE 2

DNA profile for 'ARRATWELVE'

| Microsatellite DNA Marker | Allele Sizes in Base Pairs | |
|---|---|---|
| M1 | 228 | 236 |
| M2 | 239 | 249 |
| M3 | 179 | 194 |
| M4 | 212 | 214 |
| M5 | 251 | 273 |
| M6 | 135 | 135 |
| M7 | 201 | 205 |
| M8 | 255 | 257 |
| M9 | 194 | 214 |
| M10 | 237 | 261 |

The ARRATWELVE variety has not been observed under all possible environmental conditions to date. Accordingly, it is possible that the phenotypic expression may vary somewhat with changes in light intensity and duration, cultural practices, and other environmental conditions.

Additional information relating to plant and fruit disease and pest resistance or susceptibility has not been observed to date. Specification of the plant hardiness zone and the heat/cold resistance has not been observed to date.

What is claimed is:

1. A new and distinct grapevine, botanically known as *Vitis vinifera*, identified as ARRATWELVE, substantially as shown and described herein.

* * * * *

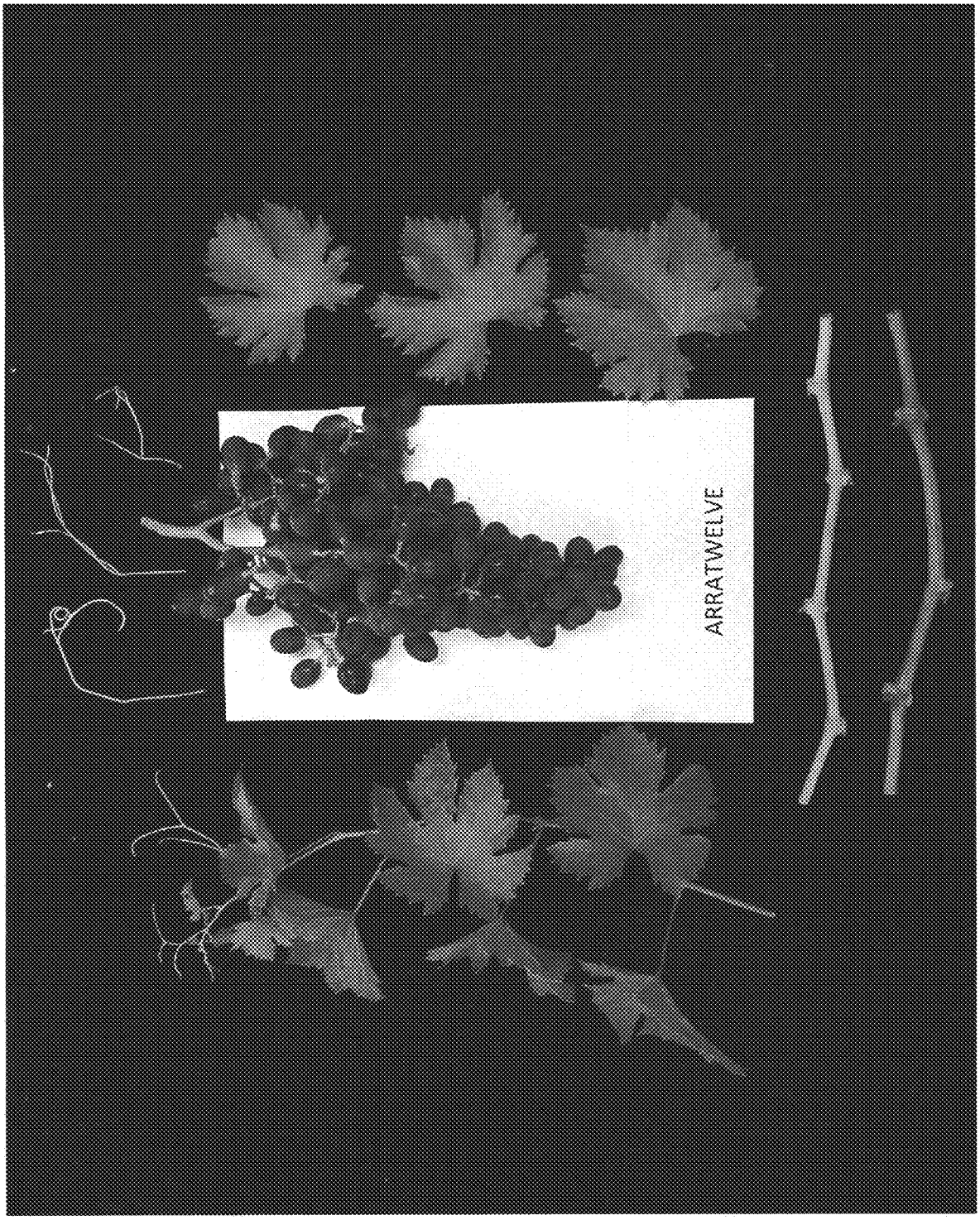
ARRATWELVE